US010422755B2

(12) United States Patent
Sones et al.

(10) Patent No.: US 10,422,755 B2
(45) Date of Patent: Sep. 24, 2019

(54) IDENTIFYING DEFECTS IN TRANSPARENT CONTAINERS

(71) Applicant: Applied Vision Corporation, Cuyahoga Falls, OH (US)

(72) Inventors: Richard A. Sones, Cleveland Heights, OH (US); Michael Leo Kress, Uniontown, OH (US); Kris Brumbaugh, Marshallville, OH (US); Kellen Reusser, Wooster, OH (US)

(73) Assignee: Applied Vision Corporation, Cuyahoga Falls, OH (US)

(*) Notice: Subject to any disclaimer, the term of this patent is extended or adjusted under 35 U.S.C. 154(b) by 100 days.

(21) Appl. No.: 15/372,047

(22) Filed: Dec. 7, 2016

(65) Prior Publication Data

US 2018/0156740 A1   Jun. 7, 2018

(51) Int. Cl.
*G01N 21/90* (2006.01)
*G01N 21/88* (2006.01)

(52) U.S. Cl.
CPC ......... *G01N 21/90* (2013.01); *G01N 21/9036* (2013.01); *G01N 2021/8845* (2013.01); *G01N 2201/0627* (2013.01)

(58) Field of Classification Search
CPC .. G01N 21/90; G01N 21/8832; G01N 21/598; G01N 2201/06153; G01N 2021/8832; G01N 2021/598; G01N 2201/0627; G01N 2021/8845; G01N 21/88; G01N 21/9036
See application file for complete search history.

(56) References Cited

U.S. PATENT DOCUMENTS

| | | | | |
|---|---|---|---|---|
| 3,980,890 A | * | 9/1976 | Heckrodt | B07C 5/34 250/223 B |
| 4,026,656 A | * | 5/1977 | Kusz | G01N 21/9036 250/223 B |
| 4,486,776 A | * | 12/1984 | Yoshida | B07C 5/126 348/132 |

(Continued)

FOREIGN PATENT DOCUMENTS

| | | | |
|---|---|---|---|
| CN | 205139027 U | * | 4/2016 |
| EP | 1617208 A1 | * | 1/2006 |

(Continued)

OTHER PUBLICATIONS

"International Search Report and Written Opinion for PCT Patent Application No. PCT/US17/65072", dated Mar. 6, 2018, 14 pages.

*Primary Examiner* — David E Harvey
(74) *Attorney, Agent, or Firm* — Medley, Behrens & Lewis, LLC (57) ABSTRACT

Described herein are various technologies related to inspecting transparent containers for both opaque and transparent defects. An emitter is configured to direct a color gradient through a sidewall of a transparent container, such that color of light that passes through the sidewall varies across the sidewall. A camera is configured to capture an image of the sidewall of the transparent container while the color gradient passes through the sidewall of the container. A computing system receives the image and determines whether the sidewall of the container includes either an opaque or a transparent defect based upon the image.

20 Claims, 8 Drawing Sheets

(56) References Cited

U.S. PATENT DOCUMENTS

| | | | | |
|---|---|---|---|---|
| 4,487,322 | A | * | 12/1984 | Juvinall ................. G01N 21/90 209/526 |
| 4,601,395 | A | * | 7/1986 | Juvinall ................. B07C 5/126 209/526 |
| 4,866,263 | A | * | 9/1989 | Fukuchi ............. G01N 21/9045 250/223 B |
| 4,915,237 | A | * | 4/1990 | Chang ................... B07C 5/122 198/406 |
| 5,004,909 | A | * | 4/1991 | Fukuchi ................ G01N 21/90 250/223 B |
| 5,095,204 | A | * | 3/1992 | Novini .............. G01N 21/9045 250/223 B |
| 5,374,988 | A | * | 12/1994 | Wertz .................... B07C 5/342 356/237.2 |
| 5,510,610 | A | | 4/1996 | Baldwin |
| 5,926,268 | A | * | 7/1999 | Bonewitz ............. B07C 5/3416 356/240.1 |
| 5,991,018 | A | * | 11/1999 | Imaizumi ........... G01B 11/0616 356/237.1 |
| 6,061,125 | A | | 5/2000 | Thomas et al. |
| 6,067,155 | A | | 5/2000 | Ringlien |
| 6,795,176 | B1 | | 9/2004 | Tennakoon et al. |
| 6,894,755 | B2 | | 5/2005 | Yu |
| 6,937,348 | B2 | * | 8/2005 | Geng ................. G01B 11/2509 356/602 |
| 6,945,662 | B2 | | 9/2005 | Diehr |
| 7,379,177 | B1 | * | 5/2008 | Sones .................... G01N 21/90 356/237.2 |
| 7,417,725 | B2 | | 8/2008 | Colle et al. |
| 7,595,870 | B2 | | 9/2009 | Ringlien |
| 7,714,824 | B2 | * | 5/2010 | Roth ..................... G09G 3/3413 345/88 |
| 7,781,723 | B1 | * | 8/2010 | Furnas ................... G01N 21/90 209/526 |
| 8,014,586 | B2 | | 9/2011 | Sones et al. |
| 8,254,659 | B2 | * | 8/2012 | Caroli .................... G01B 11/25 382/141 |
| 9,316,600 | B2 | * | 4/2016 | Kurosawa ............ B07C 5/3408 |
| 9,591,371 | B1 | * | 3/2017 | Sayre ................. H04N 21/4854 |
| 2003/0002052 | A1 | * | 1/2003 | Hoffmann .......... G01B 11/2518 356/603 |
| 2004/0263619 | A1 | * | 12/2004 | Diehr .................... G01N 21/90 348/127 |
| 2006/0221877 | A1 | | 10/2006 | Belanger |
| 2007/0102628 | A1 | * | 5/2007 | Prasad ................... G01N 21/90 250/223 B |
| 2007/0183140 | A1 | * | 8/2007 | Lusker ................ B65D 1/0223 362/154 |
| 2008/0310701 | A1 | * | 12/2008 | Caroli .................... G01B 11/25 382/141 |
| 2012/0007898 | A1 | * | 1/2012 | Pavicic ................ G09G 3/2088 345/690 |
| 2013/0215261 | A1 | * | 8/2013 | Rahmani ............... G01N 21/90 348/93 |
| 2015/0204797 | A1 | * | 7/2015 | Colle .................... G01N 21/90 356/239.4 |
| 2015/0308964 | A1 | * | 10/2015 | Schorn .................. G01N 21/90 356/240.1 |
| 2016/0077020 | A1 | | 3/2016 | Leconte et al. |
| 2016/0153919 | A1 | | 6/2016 | Smith et al. |
| 2016/0321796 | A1 | * | 11/2016 | Dordoni ................. G01L 1/24 |
| 2016/0334340 | A1 | * | 11/2016 | Ollivier ................. G01N 21/90 |
| 2018/0136142 | A1 | * | 5/2018 | Will ..................... G01N 21/8806 |
| 2018/0156740 | A1 | * | 6/2018 | Sones .................... G01N 21/958 |
| 2018/0172602 | A1 | * | 6/2018 | Beck .................... G01N 21/958 |

FOREIGN PATENT DOCUMENTS

| | | | |
|---|---|---|---|
| JP | 05-223746 A | * | 8/1993 |
| KR | 2003033678 A | * | 5/2003 |

* cited by examiner

IDENTIFYING DEFECTS IN TRANSPARENT CONTAINERS

BACKGROUND

Transparent and translucent containers, such as beverage containers, are typically inspected prior to being populated with content (e.g., liquid) and made available to consumers. For example, during manufacture of transparent or translucent containers, defects may be introduced into sidewalls of the containers. A defect that may be found in transparent and translucent containers is conventionally categorized as being one of two types; an opaque defect or a transparent defect. Opaque defects are inclusions in sidewalls of containers, wherein such inclusions are not transparent. In other words, opaque defects block light from passing therethrough. Transparent defects are those that do not block light from passing therethrough. Exemplary transparent defects include blisters (air bubbles in sidewalls of containers), wash boards (a series of horizontal waves or folds on sidewalls of containers), and checks (fine and shallow defects).

Conventionally, inspection of sidewalls of transparent and translucent containers has been performed in two stages: a first stage to detect opaque defects; and a second stage to detect transparent defects. In both stages, monochromatic LED illumination and monochrome cameras are employed in connection with detecting the transparent defects. In the first inspection stage, a backlight monochromatically directs light uniformly through the sidewall of the container, and a monochrome camera captures an image of the sidewall of the container while the light passes through the sidewall. A computing system can identify an opaque defect in the sidewall of the container based upon the image, as the defect will be depicted in the image as a dark region therein. In the second inspection stage, a backlight monochromatically directs light through the sidewall of the container in a pattern (such as a series of horizontal or vertical stripes of light). In other words, the backlight monochromatically directs light non-uniformly through the sidewall of the container, and a camera captures an image of the sidewall of the container while the backlight emits light non-uniformly. A computing system can identify a transparent defect in the sidewall of the container based upon the image, as the sidewall of the container is formed of refractive material, thereby causing the transparent defect in the sidewall of the container to be distinguishable from non-defective regions in the sidewall. It can be ascertained, however, that in the second inspection stage opaque defects may not be readily identifiable, as the image captured in the second stage includes dark regions (e.g., corresponding to dark stripes in a striped pattern).

Requiring two separate inspection stages to detect the two types of defects introduces complexities into a container inspection system. For example, in some conventional container inspection systems, separate sets of cameras are employed—one set of cameras for each inspection stage. In another exemplary conventional approach, a backlight of a container inspection system must be controlled such that it strobes between uniform lighting and non-uniform (striped) lighting. In such an inspection system, a camera captures two separate images in a short amount of time: a first image that is used to detect opaque defects; and a second image that is used to detect transparent defects.

SUMMARY

The following is a brief summary of subject matter that is described in greater detail herein. This summary is not intended to be limiting as to the scope of the claims.

Described herein are various technologies pertaining to identifying defects in transparent or translucent material. For instance, the technologies described herein are well-suited for detecting defects in sidewalls of transparent containers (such as bottles, jars, etc.), for detecting defects in decorative or utilitarian walls (such as lamp walls, vase walls, lightbulbs, etc.), etc. While the examples set forth herein refer to container sidewall inspection, it is to be understood that the technologies referenced herein are applicable to inspecting various elements composed of transparent or translucent elements.

The technologies described herein exhibit advantages over conventional container inspection systems, in that both opaque defects and transparent defects can be detected in a single inspection stage. An exemplary container inspection system described herein includes a light emitter that is configured to emit a color gradient through a sidewall of a container. In an example, the color gradient can depict a pattern (e.g., stripes, checkerboard, etc.). Put differently, at a first location on the sidewall of the container, light of a first color passes through the sidewall of the container, while at a second location on the sidewall of the container, light of a second color passes through the sidewall of the container. Further, intensity of the light can be approximately uniform (e.g., as uniform as possible). Thus, in contrast to the conventional approach where the light emitter emits light monochromatically, the light emitter in the exemplary inspection system described herein emits light of different colors, wherein different colors of light pass through the sidewall of the container at different locations.

The exemplary container inspection system also includes a camera, wherein the camera captures an image of the sidewall of the container as the light emitted by the emitter passes therethrough. As the image of the container will include no unlit regions (due to the intensity of the light being approximately uniform), a computing system can analyze the image for opaque defects. Moreover, due to light emitter directing different colors of light through different locations on the sidewall of the container, the computing system can analyze the (color) image of the sidewall of the container for transparent defects. Thus, the container inspection system has a single inspection stage for identifying both opaque and transparent defects in sidewalls of containers.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to inspection of transparent or translucent containers for both opaque and transparent defects are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Described herein are various technologies pertaining to identifying defects in transparent and translucent elements, such as container sidewalls, decorative transparent elements (such as vases, artwork, spheres), utilitarian transparent elements (e.g., light bulbs, windows, glass or plastic on television displays, etc.). An inspection system includes an emitter that is configured to direct light of multiple different colors (a color gradient) through a transparent or translucent element, such that light of different colors passes through the element at different locations thereon. A camera captures a color image of the element as the light emitted by the emitter travels through such element. A computing system analyzes the color image and can detect both transparent and opaque defects if they exist in the element based upon the image. Accordingly, the technologies described herein can be utilized to automatically identify several different types of defects that may exist in transparent or translucent elements based upon a single acquisition by the camera. The examples set forth herein refer to inspection of sidewalls of transparent or translucent containers, such as bottles or jars; it is to be understood, however, that technologies described as being applicable to container inspection are also applicable to other transparent or translucent elements, as mentioned above.

Figure 1:
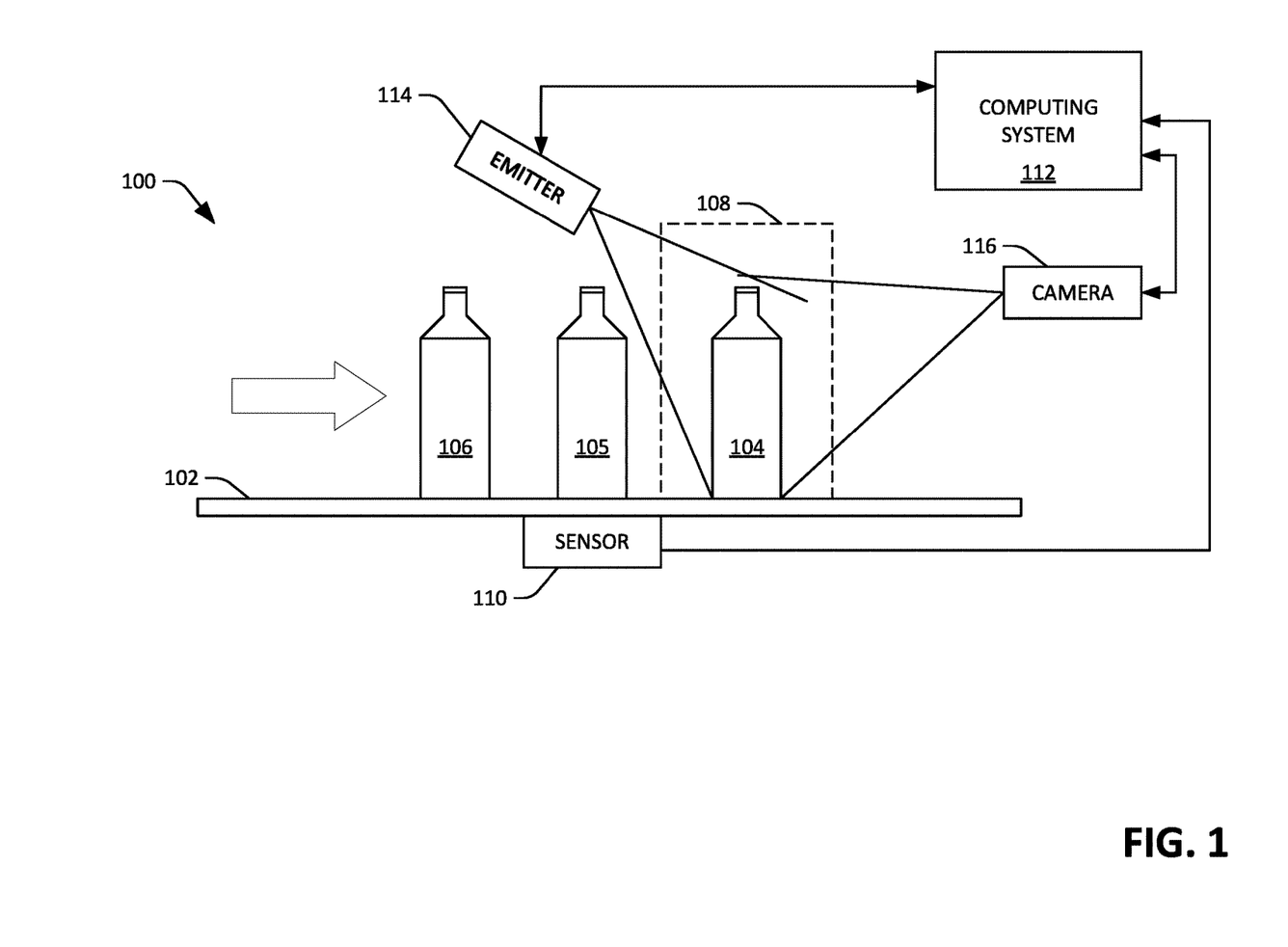
FIG. 1 is a functional block diagram of an exemplary transparent or translucent container inspection system.

With reference now to FIG. 1, an exemplary transparent and/or translucent container inspection system 100 is illustrated. For example, the system 100 can be configured to detect defects in glass containers and/or plastic containers. Further, the system 100 can be configured to detect defects in sidewalls of containers that are clear or are tinted with a hue. Finally, while the containers depicted herein have a cylindrical sidewall, it is to be understood that the container inspection system 100 can be configured to detect defects in sidewalls of varying shapes.

The container inspection system 100 can be configured to detect defects in sidewalls of containers of several types, including opaque defects and transparent defects. Exemplary opaque defects include stones. Exemplary transparent defects include blisters, checks, and wash boards. A conveyor 102 transports a plurality of containers 104-106 through an inspection region 108 of the container inspection system 100. The system 100 comprises a sensor 110 that outputs a signal that is indicative of when a first container 104 has entered the inspection region 108. For example, and not by way of limitation, the sensor 110 may be a presence sensor that can detect when the first container 104 has passed a particular point. In another example, the sensor 110 may be a rotary sensor that is configured to output data based upon movement of the conveyor 102. Thus, this data is indicative of a position of the first container 104 relative to a previous position of the first container 104 on the conveyor 102, and therefore the position of the first container 104 relative to the examination region 108.

The system 100 further includes a computing system 112 that receives the signal output by the sensor 110. The computing system 112 can receive the signal from the sensor 110 by way of a wireless or wireline connection. The system 100 further comprises an emitter 114, which is configured to direct a color gradient through a sidewall of the first container 104 when the first container 104 is in the examination region 108. In an example, the computing system 112 can control the emitter 114 such that the emitter 114 strobes light (e.g., the emitter 114 causes a flash of light of multiple colors to be emitted therefrom, responsive to the computing system 112 ascertaining that the first container 104 is in the examination region 108). In another example, the emitter 114 can be configured to continuously emit the color gradient through the examination region 108.

Generally, the emitter 114 is configured to emit light, such that light of different colors passes through different portions of the sidewall of the first container 104. For instance, in a nonlimiting example, the emitter 114 can be configured to emit primarily red light through an upper portion of the first container 104, primarily green light through a middle portion of the first container 104, and primarily blue light through a lower portion of the first container 104. In another example, the emitter 114 can be configured to emit patterns of different colored light through the first container 104 when the first container 104 is in the examination region 108. Still further, the emitter 114 can emit light with approximately uniform intensity, such that intensity of red light that passes through the sidewall of the first container 104 is approximately equivalent to intensity of green light that passes through the sidewall of the first container 104. In an alternative embodiment, the emitter 114 can cause darker colors of light directed through the sidewall of the first container 104 to have greater intensity than lighter colors of light directed through the sidewall of the first container 104. Such an approach may have advantages in detecting opaque defects at locations on the sidewall of the first container 104 where darker colored light (e.g., blue) passes therethrough.

The system 100 additionally includes a color camera 116 that is in communication with the computing system 112. More specifically, the camera 116 is controlled by the computing system 112, such that the camera 116 captures an image of a sidewall of the first container 104 when the first container is in the examination region 108 of the system 100 and when the color gradient emitted by the emitter 114 is passing through the sidewall of the first container 104. Thus, the computing system 112 receives the signal from the sensor 110 and causes the camera 116 to capture an image of the examination region 108 based upon the signal output by the sensor 110. Because the emitter 114 directs light through an entirety of the sidewall of the container 104 when the camera 116 captures the image, opaque defects are identifiable in such image. Further, as the emitter 114 directs light of different colors through different portions of the sidewall of the first container 104, an image captured by the camera 116 will visually depict transparent defects (due to refractive properties of the sidewall the first container 104).

The computing system 112 receives the image captured by the camera 116 and determines whether the sidewall of the container 104 includes a defect based upon the image. Subsequently, the computing system 112 can identify edges in the gradient image, and can compare the identified edges with signatures in a library of defect signatures. A defect signature can comprise features that are known to correspond to a defect of a three-dimensional shape, size and type. Therefore, responsive to the computing system 112 identifying an edge in the gradient image, features of such edge can be compared with a defect signature, such that it can be ascertained that the features of the edge correspond to a defect represented by the defect signature. As indicated previously, a defect signature may represent either a transparent defect or an opaque defect. Responsive to identifying a defect in the sidewall of the first container 104 based upon the image output by the camera 116, the computing system 112 can output a signal that indicates that the first container 104 includes a defect. The signal may cause, for instance, the first container 104 to be automatically removed from the conveyor 102, such that the first container 104 is prevented from being populated with content and further prevent from being made available to a consumer.

While the inspection system 100 is depicted as including a single camera and a single emitter, it is to be understood that the inspection system 100 may include multiple cameras positioned around the inspection region 108 and may further include multiple emitters positioned around the inspection region 108. Further, the emitter 114 can include several arrays of light emitters, wherein each array can include emitters that emit different colors of light. In a nonlimiting example, the emitter 114 may include multiple arrays of light emitting diodes (LEDs), wherein each array of LEDs includes LEDs that emit green light, LEDs that emit red light, and LEDs that emit blue light. The LEDs can be organized in a sequence, such as red, green, blue, red, green, blue, red, green blue, etc.

The computing system 112 can be configured to control each of the light emitters in the emitter 114 individually. Accordingly, the computing system 112 can cause the emitter 114 to emit any suitable color gradient through the sidewall of the first container 104, where the color gradient can have any suitable pattern. Further, the emitter 114 can be a backlight, wherein the emitter 114 includes a diffusing translucent material between the light emitters of the emitter 114 and the examination region 108. The use of a diffusing translucent material allows light to be approximately uniformly spread through the sidewall of the first container 104. In another exemplary embodiment, rather than the emitter 114 acting as a backlight, the emitter 114 can be placed proximate to the camera 116, and a reflective (white) material can be placed on an opposite side of the examination region 108 from the camera 116. In such an embodiment, the camera 116 captures light that is reflected from the reflective screen back through the sidewall of the container 104 when the container 104 is in the examination region 108. The process described above repeats as other containers are passed through the examination region 108 by the conveyor 102.

Figure 2:
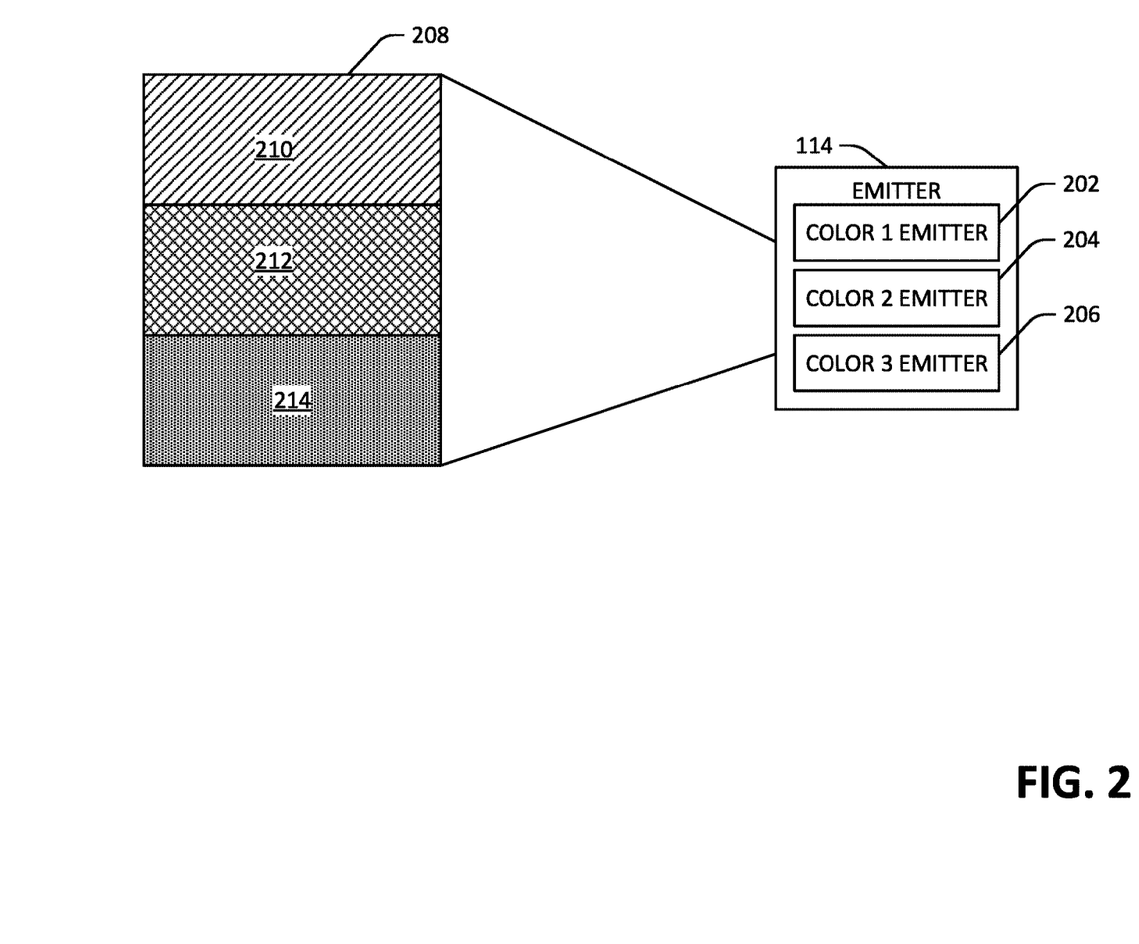
FIG. 2 is a schematic that depicts an emitter emitting a color gradient.

Referring now to FIG. 2, a functional block diagram of the emitter 114 is illustrated. As noted above, the emitter 114 can be configured to emit a color gradient through the sidewall of containers that pass through the examination region 108. As shown in FIG. 2, the emitter 114 can include multiple light emitters, each of which is configured to output light of a different color. More specifically, the emitter 114 can include a first color emitter 202 that is configured to emit light of a first color, a second color emitter 204 that is configured to emit light of a second color, and a third color emitter 206 that is configured to emit light of a third color. The emitter 114 is controlled by the computing system 112 to direct a color gradient 208 through the sidewall of the container 104. While the color gradient 208 is depicted as including three distinctive regions of light 210-214 (wherein the region 210 primarily includes light emitted by the first color emitter 202, the region 212 primarily includes light emitted by the second color emitter 204, and the region 214 primarily includes light emitted by the third color emitter 206), it is to be understood that the emitter 114 can produce a color gradient having a smooth transition between colors. Therefore, instead of discrete regions 210-214, the color gradient 208 can appear rainbow-like in an image captured by the camera 116.

Figure 3:
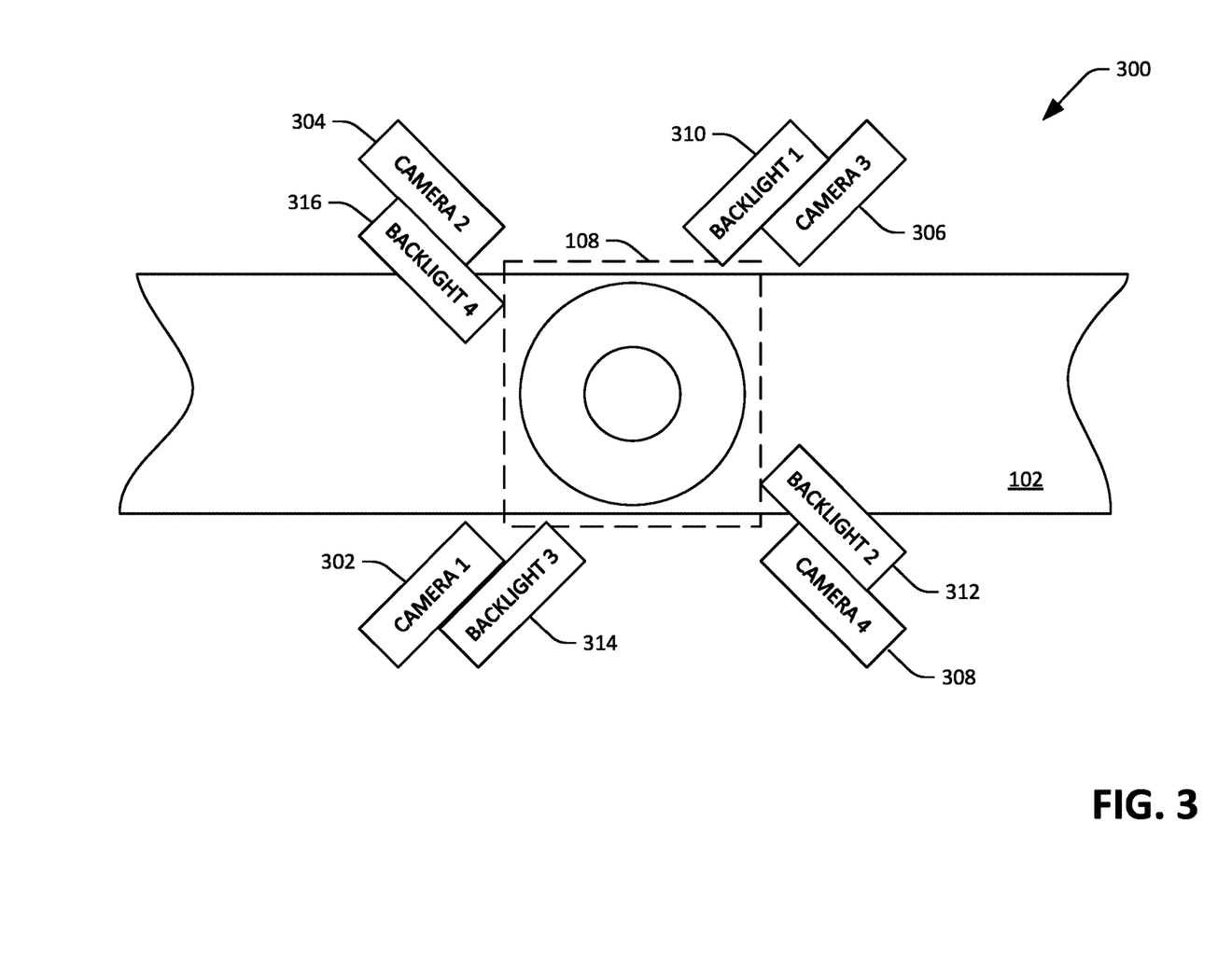
FIG. 3 is an overhead view of an exemplary transparent or translucent container inspection system.

Now referring to FIG. 3, an overhead view of an exemplary transparent or translucent container inspection system 300 is illustrated. As with the system 100, the conveyor 102 transports bottles through the inspection region 108. In the exemplary inspection system 300, a plurality of cameras 302-308 are positioned around the inspection region 108 so as to image different (all) sides of sidewalls of containers that enter the inspection region 108. While the cameras 302-308 are illustrated as being symmetrically arranged about the examination region 108, it is to be understood that the field of views of the cameras 302-308 may be offset from one another. For instance, the fields of view of the first camera 302 and the third camera 306 can be offset such that an image captured by the first camera 302 does not include the third camera 306. Moreover, the cameras 302-308 may be placed at different elevations from one another with respect to a reference plane (e.g., the plane of the conveyor 102).

The exemplary inspection system 300 further comprises a plurality of backlights 310-316 that respectively correspond to the plurality of cameras 302-308. Thus, an image captured by the first camera 302 will capture a color gradient directed through the sidewall of the first container 104 by the first backlight 310, an image captured by the second camera 304 will capture a color gradient directed through the sidewall of the first container 104 by the second backlight 312, etc. Collectively then, images captured by the cameras 302-308 when the first container 104 is in the examination region 108 depict an entirety of the exterior surface of the sidewall of the first container 104. While the system 300 is illustrated as including four cameras, it is to be understood that the system 300 may include more or fewer cameras. The system 300 may also include more or fewer than four backlights.

Figure 4:
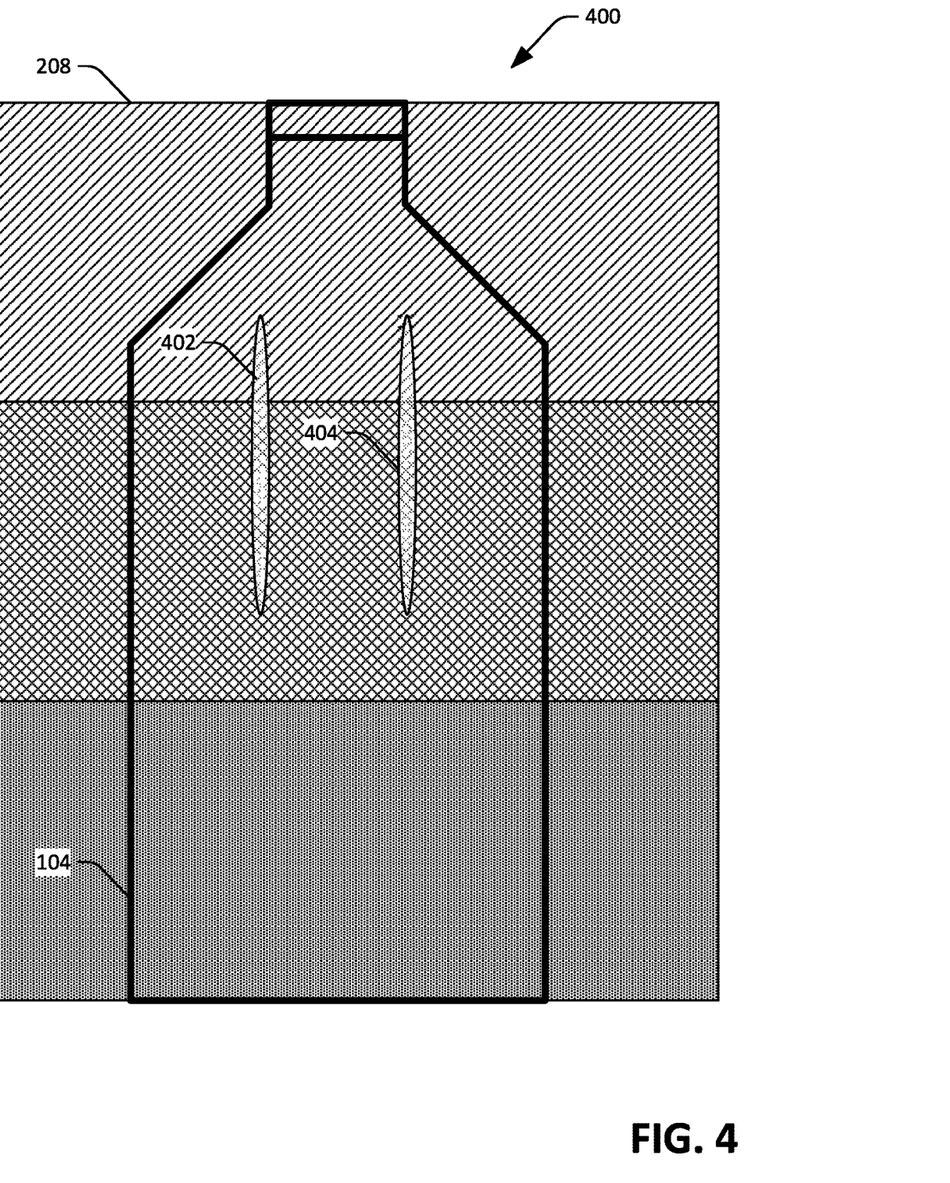
FIG. 4 depicts an exemplary image of a sidewall of a container that includes a transparent defect.

Turning now to FIG. 4, an exemplary image 400 captured by the camera 116 is illustrated. The image 400 depicts the color gradient 208 as it passes through the sidewall of the first container 104. In this example, the sidewall of the first container 104 includes two wash boards 402 and 404. Due to the first container 104 being made of material that refracts light, the wash boards 402 and 404 (which may not appear in an image illuminated uniformly by white light) are visible in the image 400; thus, the computing system 112 can detect such wash boards 402 and 404 in the sidewall of the first container 104 based upon the image.

Figure 5:
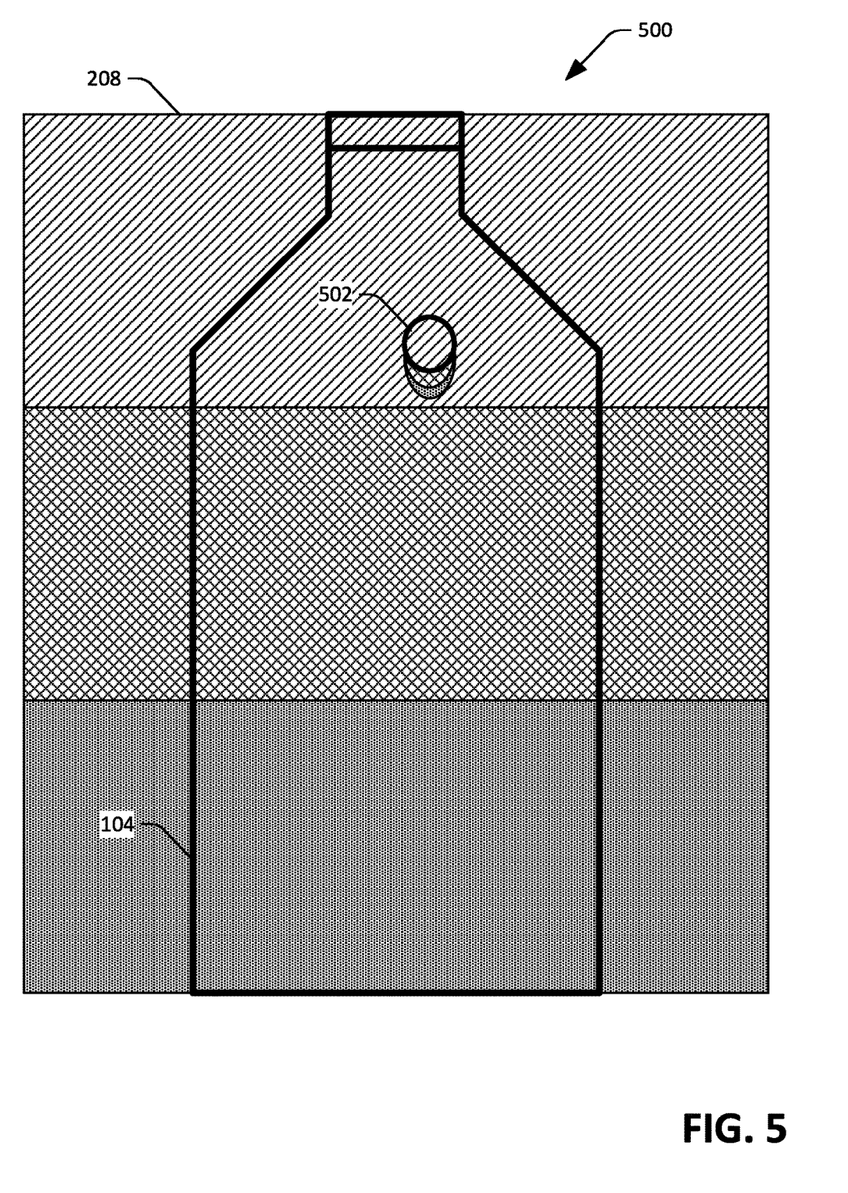
FIG. 5 depicts another exemplary image of a sidewall of a container that includes another transparent defect.

Turning to FIG. 5, another exemplary image 500 that can be captured by the camera 116 is illustrated. Again, the image 500 depicts the color gradient 208 directed through the sidewall of the first container 104 by the emitter 114. In this example, the sidewall of the first container 104 includes a blister (an air bubble) 502. As with the wash boards 402 and 404, the blister 502 may not appear in an image when white light is uniformly directed through the sidewall the container 104. Refractive properties of the sidewall of the first container 104, however, cause portions of color primarily found at the bottom of the image 500 to be represented in a lower portion of blister 502, despite the blister 502 being located at an upper region of the sidewall of the first container 104. Similarly, refractive properties of the sidewall of the first container 104, when the color gradient 208 is directed through the sidewall, can cause the blister 502 to depict color that is primarily found in a center region of the image 500, despite the blister 502 being located at an upper region of the sidewall of the first container 104.

Figure 6:
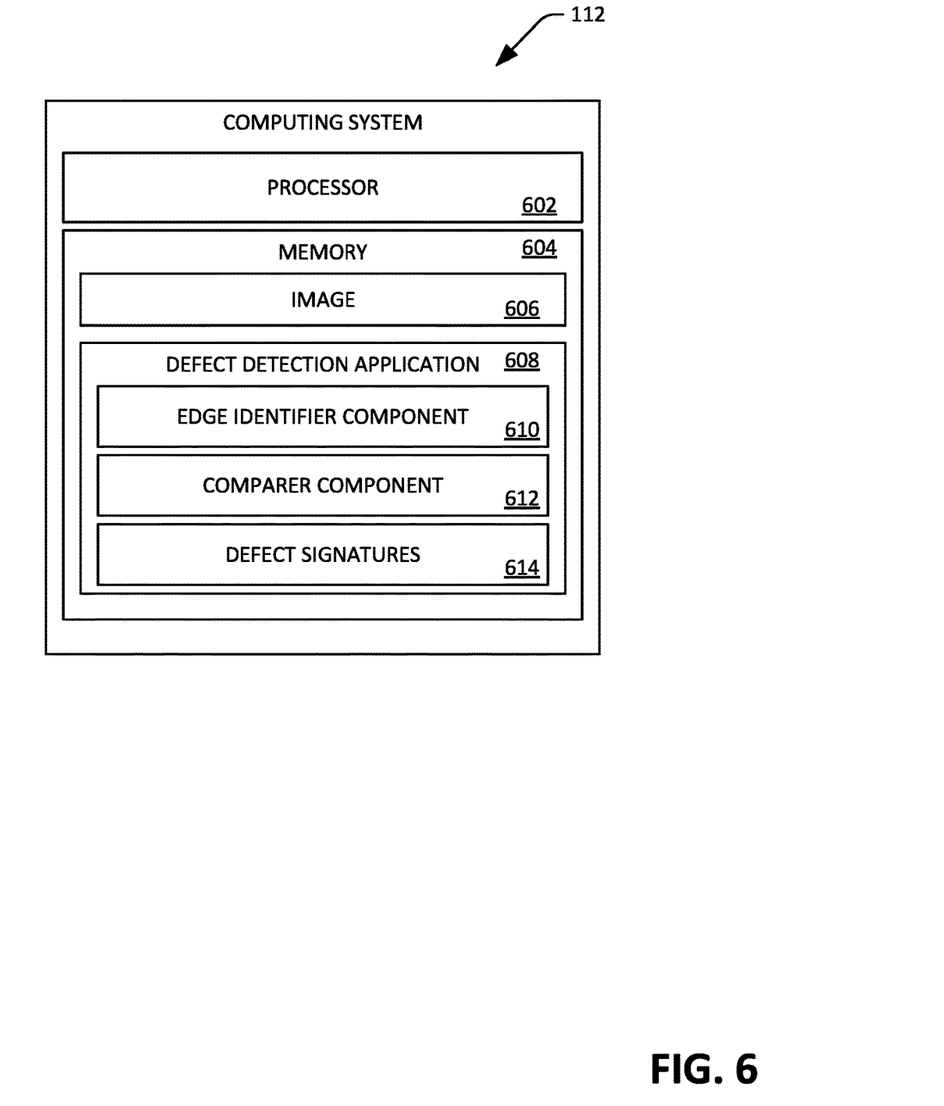
FIG. 6 is a functional block diagram of an exemplary computing system that is configured to detect opaque and transparent defects in a transparent or translucent container.

Now referring to FIG. 6, a functional block diagram of the computing system 112 is illustrated. The computing system 112 includes a processor 602 and memory 604. The memory 604 has an image 606 (generated by the camera 116) loaded therein. For instance, the image 606 may be either of the images 400 or 500. That is, the image 606 is an image of a sidewall of the first container 104 while the emitter 114 directs a color gradient through the sidewall the first container 104.

The memory 604 additionally has a defect detection application 608 loaded therein. The defect detection application 608 is generally configured to ascertain whether the sidewall of the first container 104 has a defect therein based upon the image 606. As noted previously, the defect detection application 608 can be configured to identify both transparent and opaque defects in sidewalls of containers. The defect detection application 608 includes an edge identifier component 610. The edge identifier component 610 is configured to generate a gradient image based upon the image 606, and identify edges in the gradient image. To do so, the edge identifier component 610 filters out areas in the image 606 that have a low level of contrast with respect to adjacent areas in the image (e.g., through use of a high pass filter), thereby forming the gradient image. Thus, the gradient image depicts regions in the image 606 that are in high contrast to adjacent regions in the image 606. The edge identifier component 610 can label these high contrast areas as being edges, so long as the high contrast areas have a sufficient number of pixels therein.

The defect detection application 608 also includes a comparer component 612 that is configured to compare edges in the gradient image, identified by the edge identifier component 610, with at least one defect signature in a plurality of defect signatures 614. For example, the comparer component 612 can extract characteristics of an edge detected by the edge identifier component 610 from the gradient image, such as length of the edge in the Y direction, length of the edge in the X direction, shape of the edge, etc. The defect signatures 614 can include signatures for various defects, and if the characteristics of the edge ascertained by the comparer component 612 sufficiently match a defect signature in the defect signature 614, then the comparer component 612 can output an indication that the sidewall of the first container 104 includes a defect that corresponds to the defect signature. The defect signature can be associated with various information about a defect, such as general type of the defect (e.g. transparent or opaque), specific type of the defect (blister, wash board, stone, check, etc.), three-dimensional characteristics of the defect, and so forth.

Figure 7:
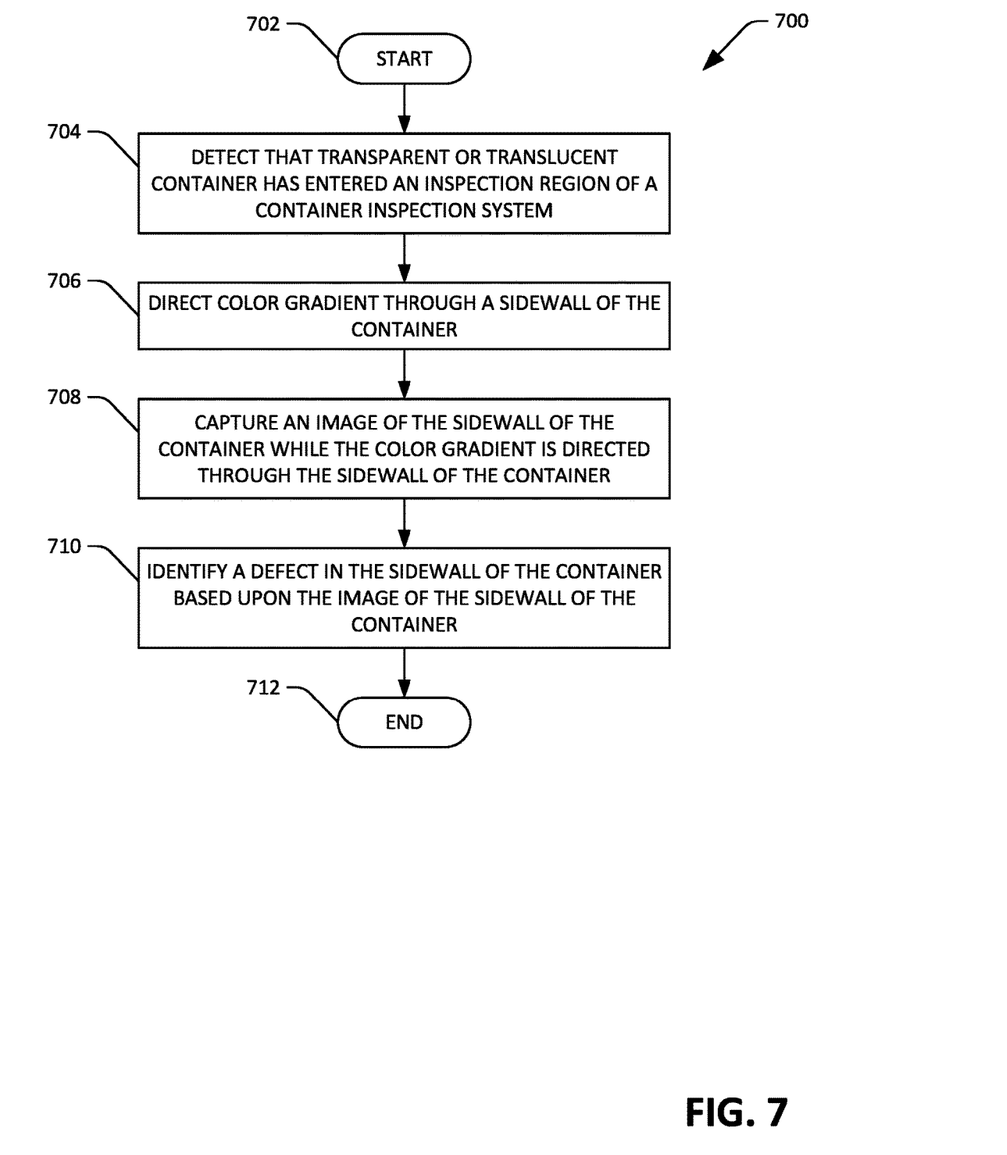
FIG. 7 is a flow diagram illustrates an exemplary methodology for identifying a defect in a sidewall of a transparent or translucent container based upon an image of the sidewall of the container.

FIG. 7 illustrates an exemplary methodology 700 relating to identifying defects in sidewalls of transparent or translucent containers. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

The exemplary methodology 700 starts at 702 and, at 704, it is detected that a transparent or translucent container has entered an inspection region of a container inspection system. As noted above, the sensor 110 can output a signal that indicates when the container has entered or is to enter the inspection region.

At 706, a color gradient is directed through a sidewall of the container. For example, the emitter 114 can be configured to direct the color gradient through the sidewall of the container, such that a rainbow-like pattern is directed through the sidewall of the container. At 708, an image of the sidewall of the container is captured, wherein the image is captured while the color gradient is directed through the sidewall the container. For instance, the camera can be configured to capture an image of the sidewall of the container when it detected that the transparent or translucent container has entered the inspection region of the container inspection system.

At 710, a defect in the sidewall of the container is identified based upon the image of the sidewall of the container. As noted above, the computing system 112 can analyze the image of the sidewall of the container to identify whether the container has either an opaque or transparent defect. The methodology 700 completes at 712.

Figure 8:
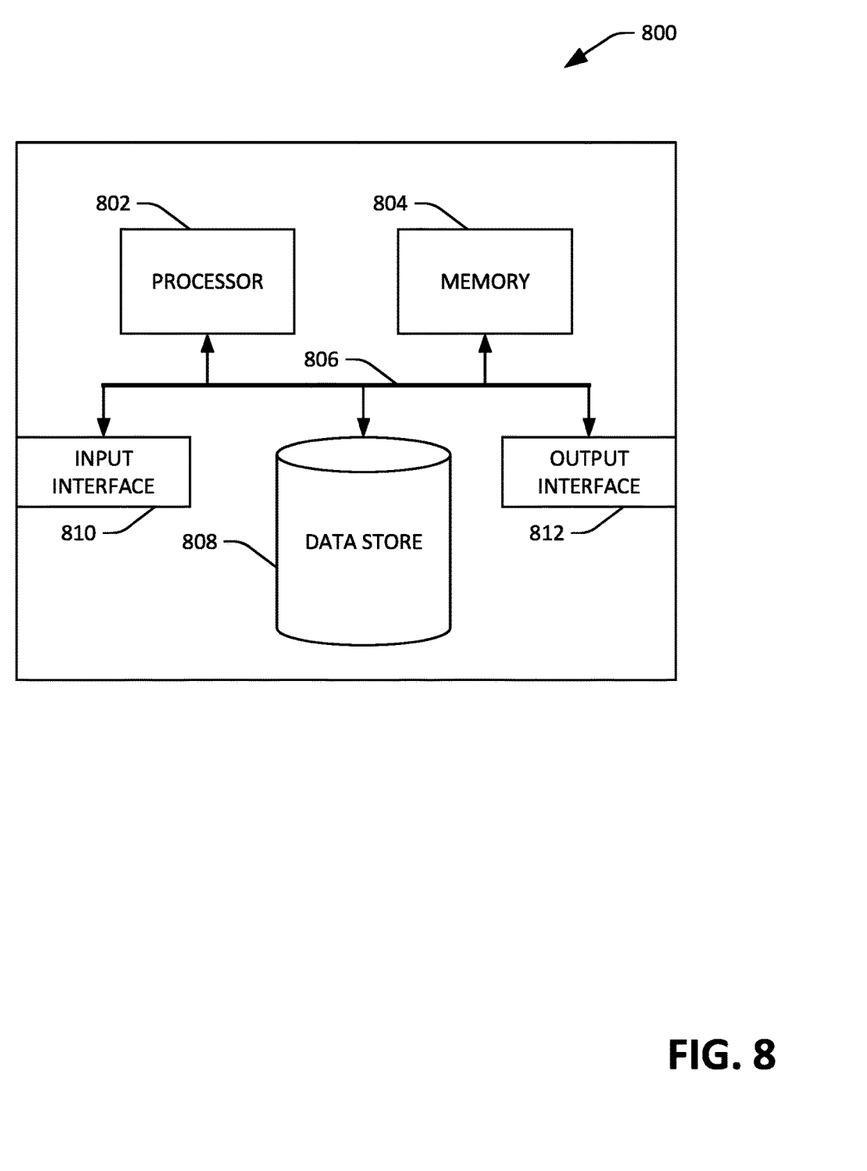
FIG. 8 is an exemplary computing system.

Referring now to FIG. 8, a high-level illustration of an exemplary computing device 800 that can be used in accordance with the systems and methodologies disclosed herein is illustrated. For instance, the computing device 800 may be used in a system that detects opaque or transparent defects in transparent containers. By way of another example, the computing device 800 can be used in a system that detects opaque or transparent defects in translucent containers. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store images, defect signatures, etc.

The computing device 800 additionally includes a data store 808 that is accessible by the processor 802 by way of the system bus 806. The data store 808 may include images, defect signatures, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that is configured to detect a defect in a transparent container, the system comprising:
    an emitter that directs light through a sidewall of the transparent container, wherein the light comprises a color gradient such that color of the light across the sidewall of the transparent container varies across the sidewall of the transparent container, and further wherein intensity of the light across the sidewall of the container is approximately uniform across an entirety of the sidewall of the container;
    a camera that is configured to capture an image of the sidewall of the transparent container while the light including the color gradient has approximately uniform intensity across the sidewall of the transparent container; and
    a computing system that is in communication with the camera, the computing system comprising a processor and memory that stores instructions that, when executed by the processor, cause the processor to perform acts comprising:
        detecting a defect in the transparent container based upon the light including the color gradient having approximately uniform intensity across the sidewall of the container as represented in the image; and outputting an indication that the transparent container includes the defect based upon the image of the sidewall of the container.

2. The system of claim 1, wherein the emitter comprises a first light emitter that emits light of a first color, a second light emitter that emits light of a second color, and a third light emitter that emits light of a third color.

3. The system of claim 2, wherein the first light emitter is a light emitting diode (LED) that emits red light, the second light emitter is an LED that emits green light, and the third light emitter is an LED that emits blue light.

4. The system of claim 2, wherein the emitter comprises a diffusing material positioned between the first light emitter, the second light emitter, and the third light emitter and the transparent container.

5. The system of claim 1, wherein the emitter is a backlight.

6. The system of claim 1, wherein the computing system is configured to detect the defect in the transparent container when the defect is a transparent defect.

7. The system of claim 6, wherein the defect is a blister.

8. The system of claim 1, wherein a conveyor transports the transparent container through an examination region of the system, and wherein the camera is configured to capture the image when the transparent container is in the examination region.

9. The system of claim 1, wherein the computing system is further configured to identify a type of the defect in the transparent container based upon the image, and further wherein the computing system is configured to output an indication of the type of the defect in response to identifying the type of the defect.

10. A method comprising:
emitting, by a backlight, a color gradient, such that the color gradient passes through a sidewall of a transparent container that is under inspection, wherein intensity of the color gradient across the sidewall of the container is approximately uniform across an entirety of the sidewall of the container;
while the intensity of the color gradient is approximately uniform across the entirety of the sidewall of the container, capturing an image of the sidewall of the container;
identifying a defect in the sidewall of the container based upon the color gradient and the intensity of the color gradient being approximately uniform across the entirety of the sidewall of the container as represented in the image; and
responsive to identifying the defect, outputting an indication that the sidewall of the container includes the defect.

11. The method of claim 10, wherein identifying the defect in the sidewall of the container comprises:
generating a gradient image based upon the image of the sidewall of the container;
identifying an edge in the gradient image;
comparing characteristics of the edge in the gradient image to a signature for the defect; and
identifying the defect based upon the comparing of the characteristics of the edge in the gradient image to the signature for the defect.

12. The method of claim 10, wherein the backlight comprises a plurality of light emitting diodes (LEDs), and further wherein the LEDs comprise first LEDs that emit red light, second LEDs that emit blue light, and third LEDs that emit green light.

13. The method of claim 10, wherein the transparent container is tinted.

14. The method of claim 10, further comprising:
identifying a type of the defect from amongst a plurality of possible types, wherein the type of the defect is identified based upon the image of the sidewall of the container.

15. The method of claim 14, wherein the type of the defect is an opaque defect.

16. The method of claim 14, wherein the type of the defect is a transparent defect.

17. The method of claim 10, wherein the container is transported on a conveyor, the method further comprising:
detecting that the container has entered an inspection region;
responsive to detecting that the container has entered the inspection region, capturing the image of the sidewall of the container.

18. The method of claim 10, further comprising:
identifying a second defect in the sidewall of the container based upon the image of the sidewall of the container, wherein the defect is a first type of defect, and wherein the second defect is a second type of defect; and
responsive to identifying the second defect, outputting an indication that the sidewall of the container includes the second defect.

19. A container inspection system that is configured to inspect transparent containers, the container inspection system comprising:
means for directing a color gradient through a sidewall of a transparent container, wherein intensity of the color gradient across the sidewall of the transparent container is approximately uniform across an entirety of the sidewall of the transparent container;
means for generating an image of the sidewall of the container while the color gradient is of approximately uniform intensity across the sidewall of the container; and
a computing system that is configured to receive the image, detect a defect in the sidewall of the container based upon the color gradient being of approximately uniform intensity across the sidewall of the container as represented in the image, and output an indication that the sidewall of the container includes the defect.

20. The transparent container inspection system of claim 19, wherein the means for directing the color gradient comprises:
first light emitting means for emitting light of a first color;
second light emitting means for emitting light of a second color; and
third light emitting means for emitting light of a third color.

* * * * *